United States Patent [19]

Bhat et al.

[11] Patent Number: Plant 5,848

[45] Date of Patent: Jan. 6, 1987

[54] CHRYSANTHEMUM PLANT NAMED HYPY

[75] Inventors: Bal K. Bhat, Hobart; Robert C. Menary, Taroona, both of Australia

[73] Assignee: The University of Tasmania, Tasmania, Australia

[21] Appl. No.: 632,330

[22] Filed: Jul. 19, 1984

[30] Foreign Application Priority Data

Jul. 20, 1983 [AU] Australia ..... PG385

[51] Int. Cl.[4] ..... A01H 5/00

[52] U.S. Cl. ..... Plt./74

[58] Field of Search ..... Plt./74

*Primary Examiner*—R. E. Bagwill

*Attorney, Agent, or Firm*—Fleit, Jacobson, Cohn & Price

[57] ABSTRACT

A new and distinct cultivar of *Chrysanthemum cinerariaefolium* plant known by the cultivar name Hypy and particularly characterized as to uniqueness as herein described and illustrated by the combined characteristics of high pyrethrins content, substantially erect growing habit and producing flowers at a substantially uniform height.

6 Drawing Figures

The present invention comprises a new and distinct cultivar of *Chrysanthemum cinerariaefolium*, hereinafter referred to by the cultivar name Hypy.

Hypy is a product of a planned breeding program which had the objective of creating new Chrysanthemum cultivars having the principle characteristics of high pyrethrins content, substantially erect growing habit, and producing flowers at a substantially uniform height. The cultivar is a stable and homogeneous variety when propagated asexually.

The new variety has been designated by the cultivar name Hypy and is referred to hereinafter as UT(P)-6. The breeder stock is held by the University of Tasmania Horticultural Research Centre, Hobart, Tasmania. UT(P)-6 is an outcome of a recurrent selection breeding program over a period of ten years. The original selections were taken from flowers grown at the University of Tasmania Horticultural Research Centre in 1979.

Details of the breeding methodology

UT(P)-6 has been developed by a recurrent selection breeding programme. The programme started with morphologically heterogeneous and genetically heterozygous population of pyrethrum. The base population consisted of individuals with highly variable morphological traits like plant height, shape and size of the flowers, maturity, canopy shape, flower yield and the pyrethrins content. For example, the range of variation in pyrethrins content, economically the most important character in pyrethrum, was noticed from 0.14 to 2.11 percent. Similar magnitude of variation was observed in other agronomically important characters also. This highly variable population was handled as follows:

Stage I

All those plants giving pyrethrins content of 1.5 percent or more of dry matter in flowers were selected and open-pollinated seed from these saved to grow the next generation. The other plants having desirable agronomic traits were also selected.

Stage II

The progeny from the open-pollinated seed of the first group of plants from stage I, i.e. high pyrethrins plants, was screened for pyrethrins content and only those plants selected which gave pyrethrins content of 1.5 percent or more.

Stage III

From stage II onwards restricted mating was enforced for 2 generations. Plants with pyrethrins content of 1.5 percent or more were allowed to interpollinate.

Stage IV

All the high pyrethrins plants from stage III were allowed to open-pollinate with plants having desirable morphological traits at stage I.

Stage V

The progeny raised from the seed from stage IV was screened for pyrethrins content, lodging resistance, flower yield and other desirable morphological traits. The screening was done in 1979 and 1980. During the 1980 screening programme one clone, bearing the selection number H80 014, was found to combine all the required characteristics. It was erect growing and showed a very high degree of lodging resistance. It produced the majority of flowers at the same height, giving high flower yield and 2.16 percent pyrethrins in the dry matter of the flowers. In fact it was the highest content of pyrethrins noticed in any clone at that stage in the entire breeding programme. Observations over the last three years in multi-location yield trials have revealed that the clone is consistent in its performance for all the characteristics mentioned above.

Asexual reproduction of Hypy pyrethrum was achieved by root splits and stem cuttings under mist propagation. For root splits the crown was vertically split into several pieces, each with a well developed shoot and root. The stem cuttings were shoots without any roots and were rooted in a mist propagation bed with bottom heat around 23±/° C.

DETAILED DESCRIPTION

In describing the colours reference has been made to the book "Methuen Handbook of colour" by A. Kornerup and J. H. Wanscher, revised by Don Pavey, Third Edition, 1978, published by Eyre Methuen, London.

Botanical: *Chrysanthemum cinerariaefolium* Vis cv. Hypy.

INFLORESCENCE

A. Capitulum (see FIGS. 4 and 5):
*Form.*—Flat.
*Type.*—Daisy.
*Diameter across face.*—50 to 65 mm.

B. Corolla of ray florets:
*General tonality.*—White, A1 (FIGS. 4 and 5).
*Color (abaxial).*—A1 (FIGS. 4 and 5).
*Color (adaxial).*—A1 (FIGS. 4 and 5).

C. Corolla of disc florets:
*Color.*—Approximately orange yellow (5B8) (unopen florets) to brownish yellow (5C8) (open florets) (FIGS. 4 and 5).

D. Reproductive organs:
*Androecium.*—Present disc florets only; abundant pollen.
*Gynoecium.*—Present both ray and disc florets.

PLANT

A. General appearance:
*Branching pattern.*—Upright dichotomous (FIGS. 2 and 3).
*Height.*—65 to 75 cm, average 71 cm.

B. Foliage:
*Color (abaxial).*—Approximately greyish geen (30E5) (FIG. 6).
*Color (adaxial).*—Approximately 30E6 (FIG. 6).

FLOWERING PERIOD

Hypy is a perennial plant and produces one flush in mid-December in southern Tasmania (42°–43° S).

Hypy can also be distinguished from other pyrethrum plants by qualitative analysis of pyrethrins in dried flowers at "¾ disc florets open stage".

This clone has been coded UT(P)-6. Its mean performance in multi-location yield trials is given in the following table and for comparison the performance of the crop raised from seed is also included.

TABLE

Performance of UT(P)-6 in comparison to seed line.

| Character | Seed line (unselected base population) | UT(P)-6 |
|---|---|---|
| 1. Flower yield (kg/ha) | 1360 | 2363 |
| 2. Pyrethrins content | | |
| a. percent | 1.31 | 2.09 |
| b. kg/ha | 17.0 | 48.0 |
| 3. 100 flowers dry wt. (g) | 17.5 | 21.3 |
| 4. No. of flowers/plant | 279 | 385 |
| 5. Stem colour | Green to purple | green |
| 6. Plant height (cm) | Variable, ranging from 54 to 100 | Average 71 |

As the crop will be grown from clonally propagated material it will be uniform and homogeneous in all the traits thus making mechanical handling a real possibility. This will enable pyrethrum to be grown as a cash crop in areas where high volume low cost labour is not available.

The most distinguishing features of UT(P)-6 are erect growing habit, lodging resistance and pyrethrins yield (kg/ha) of about three times more than the seed line.

Besides these characteristics UT(P)-6 can be readily identified by applying a sporophytic incompatibility test. This test is essentially a biochemical reaction between male (pollen) and female (stigma) parts of a flower with identical genetic constitution to prevent self-fertilization. It operates at molecular level and has been successfully employed for identification of clones in Pyrethrum (Brewer and Parlevliet, 1969, Euphytica 18: 320–325).

Method of analysis for pyrethrins

The total pyrethrins content in flowers was estimated by a slightly modified UV spectrophotometric technique of Beckly (1950) (Pyrethrum Post 2(1): 23–24).

The method consists of taking 0.5 g of finely powdered dry flowers in 25 ml volumetric flask and extracting it with petroleum ether (B.P. 40–60; aromatic free). The extraction is done for one hour in the dark. One ml of clear supernatant solution is taken in 50 ml volumetric flask and diluted with ethyl alcohol (aldehyde free) making up the final volume to 50 ml. The absorbance of this solution is read at 227 nm against a reference blank. Then the total pyrethrins (%) = A227 × 2.144. The total pyrethrins percent thus obtained is corrected for the moisture content in the powdered flower sample.

The accompanying photographic drawings show typical inflorescence and foliage characteristics of Hypy with colours being as nearly true as possible with illustrations of this type.

Figure 1:
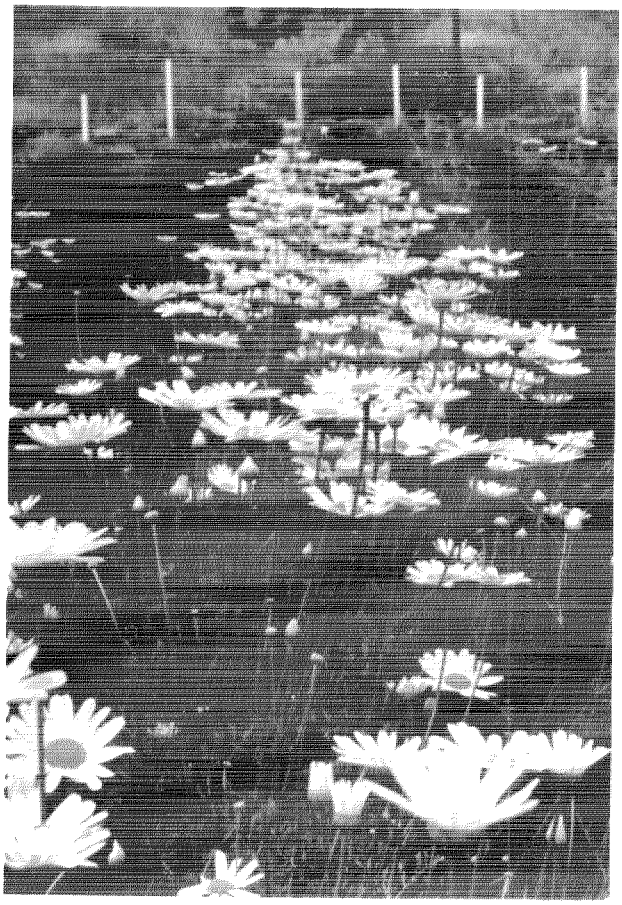
FIG. 1 illustrates a pyrethrum clone, (Hypy), growing in field showing erect growing habit and uniform flower canopy and no lodging.
Figure 2:
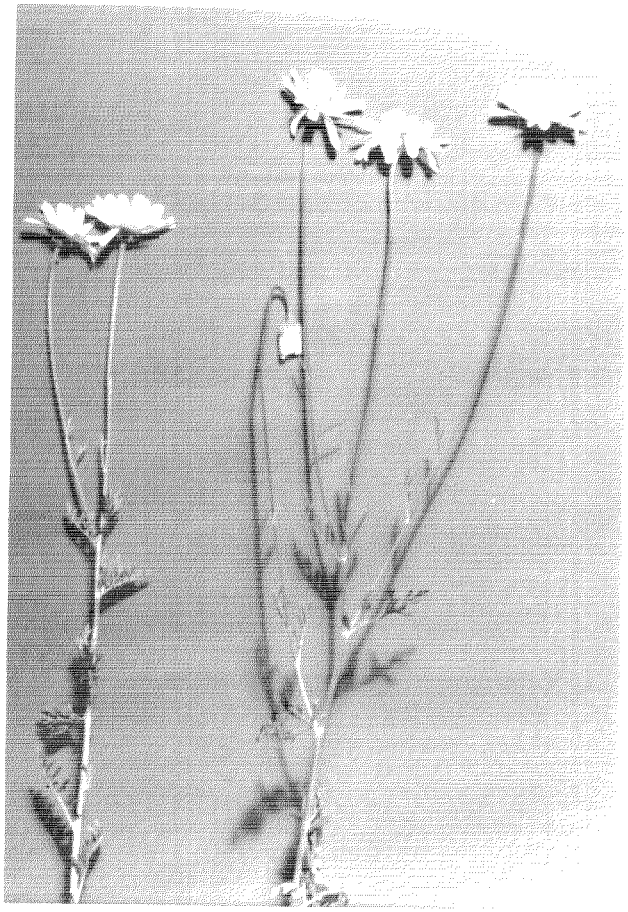
FIG. 2 illustrates the branching pattern of Hypy and the number of flowers borne on each shoot. Note the green colour of the shoots.
Figure 3:
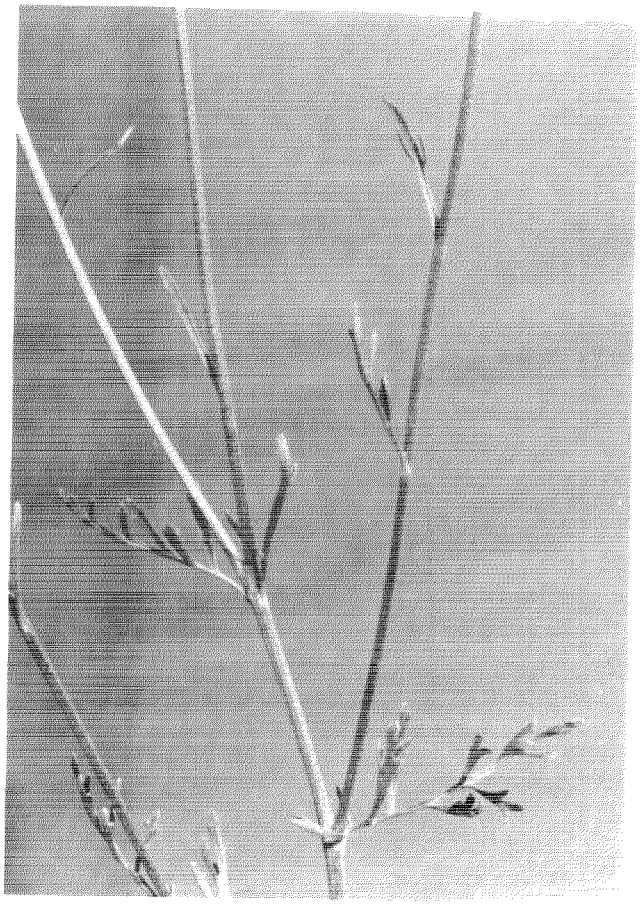
FIG. 3 is a close up of branching pattern and also showing the types of leaves borne at each node at the time of flowering.
Figure 4:
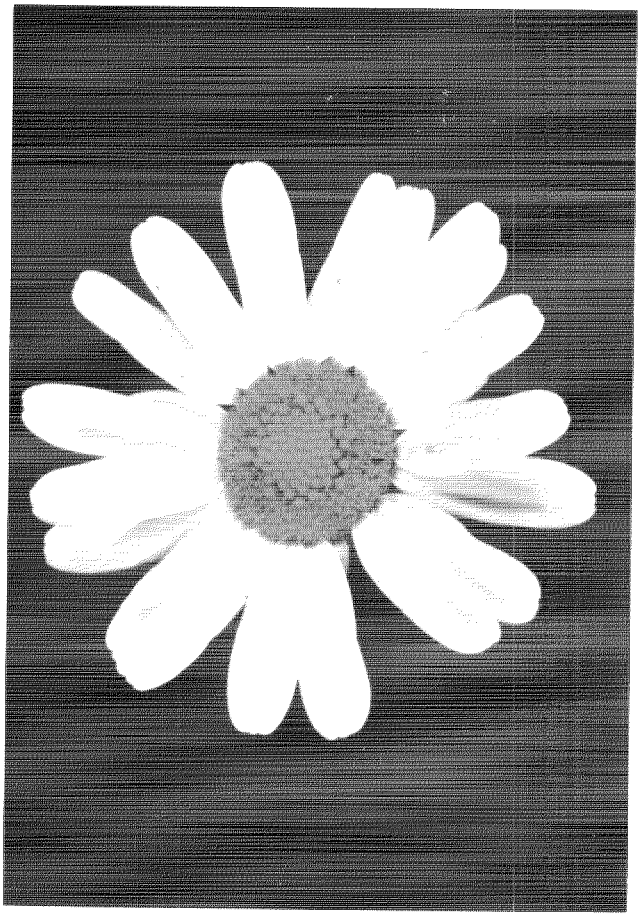
FIG. 4 is a close up of a flower at "¾ of disc florets open stage" when the pyrethrins content (%) in the flowers is at peak. Shape, size and weight of the flowers are some of the features used to distinguish clones.
Figure 5:
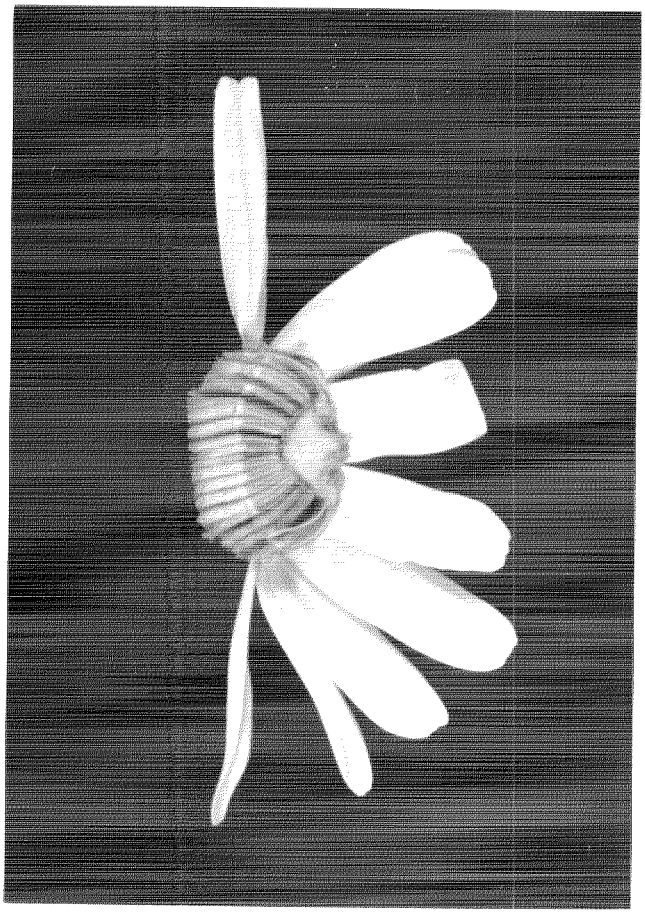
FIG. 5 illustrates a vertical section through middle of the flower showing shape of the receptacle and lengths of ovary, tubular disc floret and petals of the ray floret.
Figure 6:
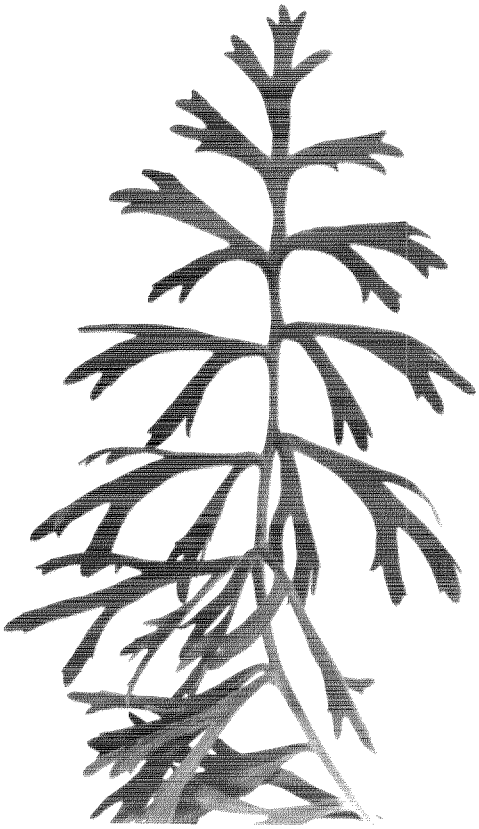
FIG. 6 illustrates the shape of the basal leaves at the time of flowering.

What we claim is:

1. A new and distinct cultivar of *Chrysanthemum cinerariaefolium* plant known by the cultivar name Hypy and particularly characterised as to uniqueness as herein described and illustrated by the combined characteristics of high pyrethrins content, substantially erect growing habit and producing flowers at a substantially uniform height.

* * * * *